(12) United States Patent
Dai (10) Patent No.: US 9,352,313 B2
(45) Date of Patent: May 31, 2016

(54) DEVICE FOR COLLECTING AND TESTING ANALYTE IN A LIQUID SAMPLE

(71) Applicant: Hangzhou Ditu Technology Co., Ltd., Zhejiang (CN)

(72) Inventor: Jielin Dai, Zhejiang (CN)

(73) Assignee: Hangzhou Ditu Technology Co., Ltd., Zhejiang Province (CN)

( * ) Notice: Subject to any disclaimer, the term of this patent is extended or adjusted under 35 U.S.C. 154(b) by 0 days.

(21) Appl. No.: 14/318,489

(22) Filed: Jun. 27, 2014

(65) Prior Publication Data
US 2015/0185240 A1    Jul. 2, 2015

(30) Foreign Application Priority Data

Dec. 31, 2013  (CN) .......................... 2013 1 0755002
Dec. 31, 2013  (CN) ....................... 2013 2 0894525 U (51) Int. Cl.
| | |
|---|---|
| *B01L 99/00* | (2010.01) |
| *G01N 33/50* | (2006.01) |
| *B01L 3/00* | (2006.01) |
| *A61B 10/00* | (2006.01) |

(52) U.S. Cl.
CPC ............ *B01L 3/502* (2013.01); *A61B 10/0045* (2013.01); *A61B 10/007* (2013.01); *A61B 10/0051* (2013.01); *A61B 2010/0006* (2013.01); *A61B 2010/0009* (2013.01); *B01L 2200/026* (2013.01); *B01L 2200/0605* (2013.01); *B01L 2200/14* (2013.01); *B01L 2300/044* (2013.01); *B01L 2300/0672* (2013.01); *B01L 2300/087* (2013.01); *B01L 2300/0832* (2013.01); *B01L 2300/123* (2013.01); *B01L 2400/0478* (2013.01)

(58) Field of Classification Search
CPC ............ A61B 10/0051; A61B 10/007; A61B 10/0045
USPC ......................................................... 422/559
See application file for complete search history.

(56) References Cited

U.S. PATENT DOCUMENTS

| | | | |
|---|---|---|---|
| 3,422,996 A | | 1/1969 | Lipman |
| 3,739,941 A | | 6/1973 | Ostrwosky et al. |
| 6,016,712 A | * | 1/2000 | Warden et al. ............. 73/864.21 |
| 6,277,646 B1 | * | 8/2001 | Guirguis et al. .............. 436/165 |

(Continued)

FOREIGN PATENT DOCUMENTS

WO    2005/023426 A2    3/2005

OTHER PUBLICATIONS

EPO Communication (Office Action) dated May 26, 2015, with an Extended European Search Report, issued by the European Patent Office in related European Patent Application No. EP-14200592.5 (7 pages).

*Primary Examiner* — Paul Hyun
(74) *Attorney, Agent, or Firm* — Osha Liang LLP (57) ABSTRACT

A device used to test the analyte in a liquid sample includes a test chamber used to contain test components, a collecting chamber used to collect liquid sample, a piston chamber between the test chamber and the collecting chamber, a piston and an opening. The piston has two positions in the piston chamber, i.e. the first position and the second position. When the piston is in the first position, liquid can flow between the piston cavity and the collecting chamber through the opening; during the piston's move from the first position to the second position, the opening is sealed by the piston, wherein while the opening is sealed by the piston, the liquid is released from the piston cavity to the test chamber. This device can help to precisely quantify a liquid sample, with higher accuracy in the tests and higher comfort during the operations.

3 Claims, 7 Drawing Sheets

(56) References Cited

U.S. PATENT DOCUMENTS

| | | | |
|---|---|---|---|
| 7,517,495 B2 * | 4/2009 | Wu | A61B 10/0045 422/550 |
| 2002/0197631 A1 * | 12/2002 | Lawrence et al. | 435/6 |
| 2003/0027359 A1 * | 2/2003 | Hudak et al. | 436/518 |
| 2013/0045501 A1 | 2/2013 | Hu et al. | |

* cited by examiner

DEVICE FOR COLLECTING AND TESTING ANALYTE IN A LIQUID SAMPLE

CROSS REFERENCE TO RELATED APPLICATIONS

This application claims the priorities of Chinese application Nos. CN 201310755002.7, filed on Dec. 31, 2013, and CN 201320894525.5, filed on Dec. 31, 2013. This application incorporates the disclosures of these prior applications by reference in their entirety.

FIELD OF THE INVENTION

The present invention relates to a testing device, specifically for testing illicit drugs in a liquid sample.

BACKGROUND

At present, the public have more and more accesses to illicit drugs, thus making such drugs more frequently used. In order to ensure a safe working environment and fair competition in sports, enterprises, institutions and sports organizations need to test the body liquids, such as urine, of their employees and athletes so in order to detect the use of such illicit drugs. Therefore, more and more devices are used in collecting and testing body liquids. Furthermore, such collections and testings are mostly performed by non-professionals in ordinary occasions, e.g. extracting a liquid sample from a container, or dropwise adding onto a chemical or immunological reagent strip. During such operations, both the samples and the tests are exposed to the open air, which may result in contamination to the environment or harm the operators.

U.S. Pat. No. 6,576,193B1 introduces a similar test device, which extracts a liquid sample for testing by relying on a piston rotating between the collecting chamber and the test chamber. Such device may leak due to the unsatisfactory closeness between the piston and the piston wall. In addition, because the sample extraction is based on piston rotations, the actual operation may cause considerable inconvenience and safety issues. In particular, during the course of rotation, it is difficult for the liquid to flow from the piston into the test chamber due to poor transfer in a confined space, which may result in an inconsistent quantity or even test failure as the sample is insufficient.

U.S. Pat. No. 7,270,959 also reveals another device for collecting and testing liquid samples. This patent states that a liquid sample is extracted relying on the horizontal motion of its piston. However, in the actual operation, the operator needs to use tremendous physical forces to move the piston. In addition, the piston handle is removable from the piston. Therefore, in practice, the piston may fail to be moved when the piston handle gets lost for certain reasons.

Therefore, there is still a need to invent a new test device that can perform a quantitative sampling for the liquid sample, with higher feasibility and accuracy. In particular, it can improve the test efficiency and accuracy in quantitativeness.

SUMMARY OF THE INVENTION

In one aspect, this invention relates to a device used to collect and test an analyte in a liquid sample, comprising: a test chamber used to contain test components, a collecting chamber used to collect liquid sample, a piston chamber between the test chamber and the collecting chamber, a movable piston set in the piston chamber. In some preferred embodiments, the moving piston transfers a portion of liquid sample from the collecting chamber to the test chamber.

In accordance with some preferred embodiments, there is a piston cavity inside the piston chamber. In accordance with some preferred embodiments, the piston, one end of the piston chamber and the wall of the piston chamber form a piston cavity, which can be used to contain a portion of the liquid sample from the collecting chamber. In accordance with some other preferred embodiments, the piston cavity comprises a piston, the wall and one end of the piston chamber, wherein the piston, the wall and an end of the piston chamber form the piston cavity.

In a preferred embodiment, the piston has two positions in the piston chamber, i.e. the first and second positions. When the piston is in the first position, liquid can flow between the piston cavity and the collecting chamber through the opening. In this way, part of the liquid sample flows from the collecting chamber into the piston cavity. While the piston moves from the first position to the second position, the opening is sealed by the piston, wherein as the opening is sealed by the piston, the liquid is released from the piston cavity to the test chamber. The process that the sample from the piston cavity is released into the test chamber and contacts the test components previously set inside the test chamber completes the analysis and test on the analyte in the liquid sample.

In some preferred embodiments, the piston consists of a puncturing component. As the piston moves from the first position to the second position, the opening is sealed, wherein as the opening is sealed, the puncturing component set inside the piston cavity pierces the puncturable material, and thus the liquid in the piston cavity is released into the test chamber through the opening of the punctured film. In accordance with some preferred embodiments, the sealing material refers to breathable and water-proof film. Thus, as the piston moves inside the piston chamber, before the film is pierced, the excessive gas (if any) will be exhausted from the piston cavity, so as to reduce the resistance in the movement of the piston and facilitate the push on the piston. Preferably, the puncturing component on the piston should be set inside the piston cavity. In accordance with some embodiments, the piston and the puncturing component are integrated to each other.

Preferably, in accordance with the embodiments above, the puncturing component is set outside the piston chamber compared with the film rather than inside the piston chamber, which also helps pierce the film.

In accordance with some preferred embodiments, the other end of the piston chamber can be sealed by a removable sealing plug. The piston comprises an ejecting structure on the top, such as a non-piercing shape at the top of the puncturing component. When the piston moves inside the piston chamber, as it seals the opening hereof, this ejecting structure pushes the sealing plug out from the other end of the piston chamber, and thus a portion of the liquid sample is released from the piston cavity into the test chamber. In accordance with some preferred embodiments, the sealing plug is made of silica gel, rubber and/or plastics.

In accordance with some other preferred embodiments, one end of the piston chamber is made of a puncturable sealing material, and can be sealed by some film. Such film may be an aluminum foil, adhesive film or plastic film, which can keep the formed piston cavity in a confined space, except the liquid communication with the collecting chamber through the first passage. However, these films can be easily pierced.

In accordance with some other preferred embodiments, when the piston moves from the first position to the second position, the piston seals the opening set between the piston cavity and the collecting chamber with its outer edge, wherein the piston continues its motion inside the piston cavity. During such motion, the piston remains sealing the first passage with its out edge. Preferably, the piston that continues its motion in the piston cavity compresses the volume of the latter, so as to force the liquid sample to flow into the test chamber. It is preferable to set one or more grooves on the outer edge of the piston, and resilient rings inside the grooves hereof. The resilient sealing rings keep the space between the outer edge and the inner wall of the piston in a confined state. Preferably, as the outer edge of the piston seals the first passage, two said sealing rings are involved, set on both ends of the passage. In accordance with some other preferred embodiments, the thickness or length of the outer edge equals the depth of the piston cavity. When the piston is at the first position, one end of the piston is close to the first passage, and the other end is in the piston chamber, but not in the piston cavity. When the piston is at the second position, the one end close to the first passage is inside the piston cavity, with its outer edge sealing the passage. Thus, the piston fills the entire piston cavity and compresses the liquid sample herein substantially into the test chamber.

In accordance with some preferred embodiments, one end of the piston chamber is sealed with a puncturable film. Such film is certainly resilient. When the piston moves inside the piston chamber, especially when the piston cavity is filled with the liquid sample, the piston moves toward one end of the piston chamber and forces the liquid sample to transfer into the piston cavity. In order to make the piston to move from the first position to the second position, the film should be resilient to some extent. Thus, as the piston moves to the second position, the resilient film sealing the other end of the piston chamber bloats. Meanwhile, the puncturing component set outside the piston cavity pierces the bloated film, and releases the liquid sample from the piston cavity into the test chamber. Of course, as the resilient sealing film exists, once the sealed piston opens, the puncturing component may pierce the film, or the piston continues to move and bloats the film, so as to be pierced by the puncturing component outside. When the outer edge of the piston opens, as sealed, the puncturing component pierces the film. In this case, the piston continues to move, and forces all the liquid sample to flow from the piston cavity into the test chamber through the pierced film. At this time, the opening is still sealed by outer edge of the piston, and the volume of piston cavity reduces and even to 0.

In another aspect, the present invention relates a device used to test the analyte in a liquid sample, comprising: a test chamber used to contain test components, a collecting chamber used to collect liquid sample, a piston chamber between the test chamber and the collecting chamber, a piston and an opening. The piston has two positions in the piston chamber, i.e., the first position and the second position. When the piston is in the first position, liquid can flow between the piston cavity and the collecting chamber through the opening. While the piston moves from the first position to the second position, the opening is sealed by the piston, wherein as the opening is sealed by the piston, the liquid is released from the piston cavity to the test chamber.

Preferably, the piston chamber has openings on both ends, one of which is sealed by the piston, and the other is sealed by sealing material. Preferably, the sealing material is puncturable and the piston is structured with a puncturing component. As the piston moves from the first position to the second position, the opening set between the piston cavity and the collecting chamber is sealed. In the meanwhile, when this opening is sealed, the puncturing component pierces the puncturable sealing material, and releases the liquid from the piston cavity into the test chamber through the sealing material. Preferably, the puncturable sealing material is breathable and water-proof.

Preferably, the sealing material is resilient and puncturable. As the piston moves from the first position to the second position, the resilient material bulges outward on the other end of the piston chamber, and then the projected resilient sealing material is pierced by the puncturing component. Thus, the liquid sample is released from the piston cavity into the test chamber through the pierced material. Preferably, the puncturing component is set on the outside of the piston chamber, facing the resilient and puncturable material hereof.

Preferably, the piston chamber has an opening on each end, one of which is sealed by the piston, and the other is sealed by a sealing plug. The piston is structured with an ejecting component. As the piston moves from the first position to the second position, the opening set between the piston cavity and the collecting chamber is sealed, wherein when is opening is sealed, the ejecting component pushes the sealing plug out, and thus releases the liquid from the piston cavity into the test chamber through the pushed-open end. Preferably, the sealing plug is made of silica gel.

In accordance with all of the foregoing embodiments, preferably, the opening set between the piston cavity and the collecting chamber is sealed by the piston with its outer edge.

In accordance with all of the foregoing embodiments, preferably, after the opening set between the piston cavity and the collecting chamber is sealed by the piston with its outer edge, the piston will continue to move inside the piston chamber, and thus compress the volume of the piston cavity.

In accordance with all of the foregoing embodiments, preferably, the length of the piston equals the depth of the piston cavity in essence. When the piston remains at the first place, one end of the piston gets close to the opening between the piston cavity and the collecting chamber without getting it sealed. The other end of the piston remains inside of the piston chamber and stays far away from the opening between the piston cavity and the collecting chamber.

In accordance with all of the foregoing embodiments, preferably, the opening between the piston cavity and the collecting chamber is 3-8 mm wide.

In accordance with all of the foregoing embodiments, preferably, the piston hereof is featured with a groove, with resilient sealing rings set inside, so as to seal the piston and the inner wall of the piston chamber.

In accordance with all of the foregoing embodiments, preferably, the piston cavity is formed by the piston, part of the wall of the piston chamber and the opening on the other end of the piston chamber.

In accordance with all of the foregoing embodiments, preferably, the test chamber is set with testing components inside. The liquid sample is urine.

In accordance with all of the foregoing embodiments, preferably, the first passage or opening is set on the wall of the piston chamber. Thus, the liquid in the collecting chamber maintains communication with the piston cavity through the first passage.

In accordance with all of the foregoing embodiments, preferably, the piston is integrated with a piston rod, which is pushed by external forces so as to get the piston to move inside the piston chamber. The external force can be manually driven or provided by automatic piston rod in an automatic mechanical structure.

In accordance with all of the foregoing embodiments, preferably, the piston push rod is featured with a stop component, which can set the initial position of the piston in the piston chamber, so as to avoid any liquid extraction and test caused by a mistaken push. Preferably, the stop component is a snap ring, and can be removed from the push rod.

In all of the foregoing embodiments, preferably, there is one or more test components inside the test chamber. Preferably, the test components includes immune test strips and adulteration test strips. Preferably, the absorbent pad is close to the bottom of the test chamber.

BENEFICIAL EFFECTS

The present invention can help achieve the automatic extraction and test of liquid samples, with an accurate quantitative sampling. In addition, it is easy for both operation and production, and thus increases the test efficiency.

DETAILED DESCRIPTION

The following explanation made for the structures of the present invention or the technical terms are not intended to limit the scope of the present invention.

Testing

Testing is to analyze or detect the existence of a substance or a material, such as, but are not limited to, chemicals, organic compounds, inorganic compounds, metabolites, drugs or drug metabolites, organism and organism metabolites, nucleic acid, protein, or polymer. In addition, testing also refers to quantifying the substance or material. Further, testing refers to immunoassay tests, chemical tests, and enzymatic detection, etc.

Sample

A sample in the present invention refers to a substance with which the existence of certain interesting substance can be tested, analyzed or diagnosed in an analyte. For example, a sample can be a liquid sample, such as blood, plasma, serum, urine, saliva, and various exudates, or a solution transformed from a solid sample or semi-solid sample after pre-treatment. The collected sample can be used for testing the presence of an analyte with such methods as immunoassay, chemical detection and enzymatic detection, etc.

A sample can be in liquid, which includes various kinds of body fluid, such as blood, serum, plasma, saliva, urine, tears, semen and marrow; a liquid sample can be a water sample, such as sea water, river water, household water, municipal water, industrial water, runoff water and sewage.

Analyte

The present invention relates to a device and methods to analyze all analytes, and the analytes can be detected in all liquid samples or liquefied samples, such as urine, saliva, saliva, blood, plasma or serum.

An analyte in accordance with embodiments of the present invention can be "drugs of abuse" (DOA) or any other interesting substance(s) in the sample. "Drugs of abuse" (DOA) refer to the drugs for non-medical purpose (often with nerve paralysis effect). The abuse of such drugs can cause physical and mental damages, leading to dependency, addiction and/or death. Typical examples include cocaine and amphetamine (such as Black Beauty, White Benny). Such drugs can break down into different small molecules once absorbed by the body, which exist in blood, urine, saliva, sweat and other body liquids, or the small molecules are present in part of the body liquid(s).

Testing Components

A device in accordance with embodiments of the present invention can employ a variety of test strips, which is determined by the analyte and the test purpose. The test strips can be roughly divided into two categories: detection test strip and adulteration test strip. The former is to test the composition of a test sample; the latter is to test the substance with a certain nature contained in a test sample. Both categories consist of loading zone and test zone.

Detection Test Strip:

Various detection test strips can be adopted in accordance with embodiments of the present invention. Detection test strips are used for immunoassay, chemical detection and testing for an analyte in a test sample. Such analytes involve drugs of abuse, or metabolites that can imply one's health state.

For example, a "drugs of abuse" (DOA) described above are legal for medical purpose, but prone to overdose, and can be detected with a test strip of the present invention. Such drugs include tricyclic antidepressants (imipramine and its analogues) and OTC products containing acetaminophen (such as pharmaceuticals trademark Tylenol provided by McNeil-PPC, located in Washington, Pa. Such test can help emergency personnel determine whether a patient in a coma has accidentally overdosed any of these drugs.

Detection test strips may be in various forms. In general, test strips are made of absorbent materials, which consist of loading zone, raw material zone and test result zone. A sample is added to the loading zone, moistens the raw material zone by capillary forces, dissolves and mixes the raw materials needed by the analyte at the raw material zone (if any in the sample). The mixed raw material sample continues to moist the test result zone, and the extra material is immobilized in the test result zone. These materials react with the analyte (if any) or one of the materials of the first group in the raw material zone. If the analyte does exist in the sample, a signal will appear in the test zone; otherwise, it will not.

In a more specific embodiment: the following detection test strips revealed in materials published in the following US patent or patent application numbers can be used in this invention: U.S. Pat. Nos. 5,252,496, 5,415,994, 5,559,041, 5,602,040, 5,656,503, 5,712,170, 5,877,028, 5,965,458, 6,046,058, 6,136,610, 6,140,136, 6,183,972, 6,187,268, 6,187,598, 6,194,221, 6,194,224, 6,221,678, 6,228,660, 6,241,689, 6,248,598, 6,271,046, 6,297,020, 6,316,205, and 6,372,514.

Adulteration Test Strip:

Adulteration test strips aim to test a physical characteristic of a test sample or a contamination, such as temperature, specific gravity, pH, oxidant pollution, glutaconaldehyde pollution, nitrite pollution, ascorbic acid vitamin C pollution and creatinine contamination. For this test purpose, it is advisable to adopt the following test strips. These test strips have combined the reagents used to test extra chemicals or compromise a test result and conceal a drug taking behavior due to other reasons.

The test strips for testing the material properties of a liquid sample can be used with embodiments of the present invention. Such strips include absorbent materials for transporting liquid samples through the test strips, filter components in liquid communication with absorbent materials, a raw material pad in liquid communication with the filter components, and an optional transparent lid. A raw material pad comprises the raw material used to produce a detectable symbol, which is associated with the feature(s) of the sample, and observable through the transparent lid and the transparent plate of this device (if applied). A filter component can be made of the material(s) capable of prohibiting liquid(s) from flowing from the raw material pad back to the absorbent material.

"Prohibition of reflux" refers to the liquid flowing from the raw material pad to the absorbent material is in such a small quantity that it will not change the test result, or the quantity of the raw material transferred from the raw material pad to the absorbent material or to the adjacent raw material pad is so small that it cannot be detected or will not lead to any unclear result.

The test strips can also include some immoistenable materials set between part of the filter materials and the absorbent materials. Such immoistenable material is for purpose of prohibiting the reflux of the sample from the raw material pad to the absorbent material. The liquid sample is transmitted through the entire test strip by the capillarity action, which refers to a physical effect well known to technical personnel that is generated through an interactive reaction between a liquid and a wall or material, and this physical effect can cause liquids to be transmitted through the material.

"Absorbent material" refers to the material that can easily attract or absorb liquids, and is suitable for capillarity action to guide liquids from one point to another point of this material.

"Filter component" can facilitate a uniform diffusion of the sample when it flows to the raw material pad, so as to form detectable symbols in proper order and in a homogenous manner. In the meanwhile, a filter component can also prohibit the sample from flowing from the raw material pad back to the absorbent material. In turn, it can prevent the chemical substances of the raw material from being transferred from one raw material pad to another.

"Immoistenable material" refers to the material that does not allow any quantity of the liquid that can change the test result to flow through, and often serves as a liquid flow barrier.

Piston and Piston Chamber

In accordance with some specific embodiments, a piston chamber 100 can be in the shape of a cylinder. The middle of the cylinder is hollow, which is the cavity of the piston chamber, and both ends of the piston chamber are open. A piston 200 is inserted from an opening 104 of the piston chamber 100 into the piston chamber 100. An outer edge 201 of the piston 200 contacts an inner wall 102 of the piston chamber 100, so as to seal the opening 104 of the piston chamber 100, and keep the liquid sample in the piston chamber without spill-over.

In accordance with another embodiment, the outer edge 201 of the piston 200 is structured with grooves 204 and 203. An resilient sealing ring 501 is set above the grooves. The resilient sealing ring 501 contacts the inner wall 102 of the piston 200, so as to achieve a sealing effect. The number of sealing rings can be 1, 2 or larger, and can be set separately above the grooves. When the piston 200 is thick enough, the grooves can be set at both ends 202 and 205 of the outer edge of the piston, with a sealing ring 501, respectively, installed in both grooves 203 and 204. Such sealing can at least prevent the liquid sample in the piston chamber from leaking between the outer edge 201 of the piston and the inner wall 102 of the piston chamber. In addition to such sealing method, a bolt, a snap or other forms can also be used to seal between the piston 200 and the piston chamber 100.

The other end 101 of the piston chamber is sealed by the sealing material 900 that can be easily pierced, such as puncturable sealing fin, puncturable double-sided adhesive, or other puncturable films, including aluminum foil, thin plastic sheet and so on. In addition, the sealing material 900 used to seal the other end 101 of the piston chamber can also be breathable, water-proof and puncturable. The sealed end 101 of the piston chamber, the other end 205 of the piston 200, and the inner wall 103 of the piston chamber collectively form the piston cavity 70, which receives part of the liquid sample from the collecting chamber 80 through the opening 103. In the meanwhile, the piston cavity 70 also transfers the liquid sample inside the collecting chamber 80 to the test chamber 10 through the motion of the piston. Thus, the piston cavity 70 is restrained by the other end 205 of the piston 200, the end 101 of the piston chamber 100 and the wall 103 of the piston.

Figure 1:
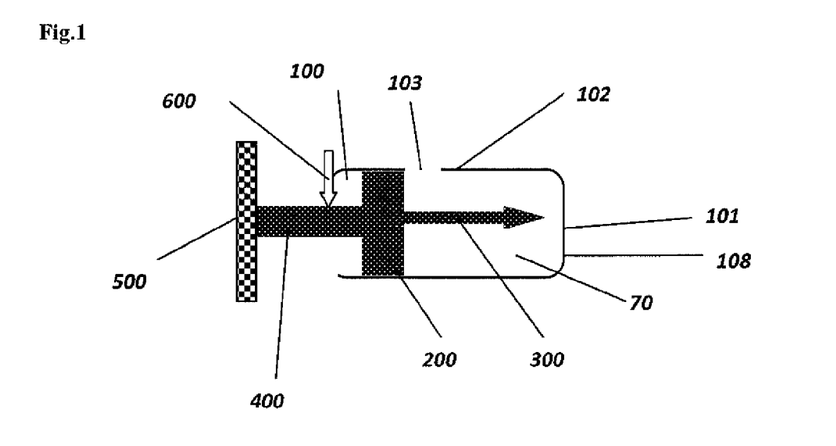
FIG. 1 shows a schematic view of an embodiment in accordance with the present invention (the piston is at the first position)
Figure 4:
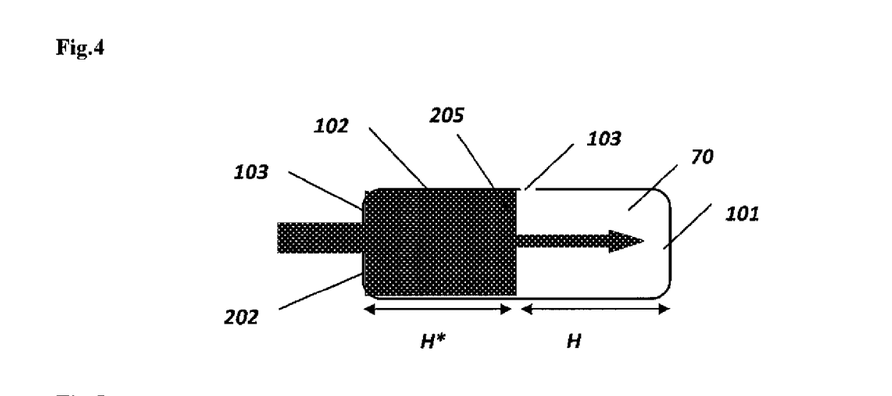
FIG. 4 shows a schematic view of another embodiment in accordance with the present invention.

In accordance with some embodiments, in order to urge a smooth access of part of the liquid sample from the collecting chamber to the piston cavity 70, an opening 103 or a passage on the wall of the piston chamber is set so as to achieve a liquid communication between the collecting chamber 80 and the piston cavity 70. Thus, when there is any liquid sample collected in the collecting chamber, it will be released the piston cavity or even fill the piston cavity through the opening or passage without difficulty. In order to accelerate an accurate flow of the liquid sample from the collecting chamber 80 into the test chamber 10, the piston 200 at the initial state is generally set next to the opening 103, or leaves the opening or the passage semi-sealed. Thus, when any liquid sample is collected in the collecting chamber, thanks to the liquid communication between the opening 103 and the piston cavity 70, the liquid sample will be naturally released from the collecting chamber into the piston cavity. At this time, the piston is located at the first place (see FIGS. 1 and 4). As the puncturable sealing fin, the double-sided adhesive or other films seal the other end 108 of the piston cavity 70 (at this time, part of the space in the piston chamber 100 is confined to be the piston cavity 70, and the other end 101 of the piston chamber has naturally become the bottom 108 of the piston cavity 70), a puncturing component 300 is set on the piston 200, and this puncturing component can pierce the sealing material 900 used to seal the other end of the piston chamber.

In accordance with some embodiments, this puncturing component 300 is set inside the piston cavity 70 and on the piston 200. In addition, we set the distance between the piercing end 301 of the puncturing component and the sealing material 900 or the other end 101 of the piston chamber smaller than or equal to the length of the opening on the piston chamber. When the piston 200 moves toward the other end 101 of the piston chamber inside the piston chamber 100, once the outer edge 201 of the piston substantially and completely seals the opening 103, the puncturing component 300 pierces the sealing material 900 that seals the other end 101 of the piston chamber 100, so that the liquid sample is released immediately from the piston cavity 70 into the test chamber through the pierced sealing material. The liquid sample in the test chamber 10 contacts the test component 20, and thus the opening 103 is sealed and the sealing material 900 is pierced virtually at the same time. "Virtually" sealing the opening 103 herein means the opening is sealed by the outer edge of the piston, preventing the liquid sample returning from the collecting chamber 80 into the piston cavity 70. In general, as the piston is pushed at a high speed, the opening is sealed and the sealing material is pierced at the same moment, which increases the working efficiency. Especially, during manual operation, the comfort can be improved.

In accordance with another preferred embodiment, the sealing material 900 used to seal one end of the piston chamber is breathable and water-proof. In other embodiments, such breathable and water-proof materials can be easily puncturable.

In accordance with other embodiments, the sealing material 900 used to seal the end 101 of the piston chamber is not sealing film that can be easily pierced, but a plug, such as a silica gel plug. When the piston 200 moves inside the piston cavity 70 or the piston chamber 100, the outer edge 201 of the piston 100 seals the opening 103 (the opening or passage between the piston cavity and the collecting chamber). In the meanwhile, the push rod set on the piston 100 and inside the piston cavity (the puncturing component does not have a sharp tip but non-sharp top) moves forward together, and pushes out the plug (which also seals one end of the piston chamber) sealing the bottom 108 of the piston cavity 70, so as to make the liquid sample flow from the piston cavity into the test chamber. The effect of adopting a plug is better than piercing the sealing material, because after the plug is pushed out, the bottom of the piston cavity is virtually completely opened, which facilitates the flow of the liquid sample into the test chamber, while the puncturing component usually pierces a small opening, then tears it open, in which case it is difficult for liquid to flow out of the piston cavity, compared with the scenario sealed with a plug.

In another preferred embodiment, when the piston 200 moves inside the piston chamber 100, the volume of the piston cavity 70 can be compressed. If the sealing material at the other end of the piston chamber is resilient (See FIG. 8, wherein the dotted line presents the uncompressed state of the resilient materials), the piston moving can cause such resilient material 90 to raise outwardly, so as to compress the volume of the piston cavity (in specific ways as described above). In these embodiments, the puncturing component 300 does not have to be set inside the piston cavity, but on the outside (See FIG. 8). When the piston is at the initial position, the sharp tip 301 of the puncturing component is set next to the sealing component, without piercing it. At this time, the resilient component can form a slight projection as the result of overcoming the pressure of the liquid, and such projection fails to be substantially pierced. When the piston 200 moves inside the piston cavity 70, once the outer edge 201 of the piston seals the opening 103 between the piston cavity 70 and the collecting chamber 80, the instant when the opening is sealed, the entire piston cavity enters into a confined state. The piston will continue to move a little more forward by, say, 1-2 mm, which may be due to the inertia of the piston movement. Thus, the piston 200 compresses the volume of the piston cavity 70, and the resilient material projects toward the outside of the piston cavity due to the outer forces (see FIG. 8). Once the projecting part contacts the puncturing tip of the puncturing component, the resilient material is pierced, and the liquid sample is released from the piston cavity into the test chamber. Such resilient material is also easily puncturable, such as thin rubber films.

Figure 5:
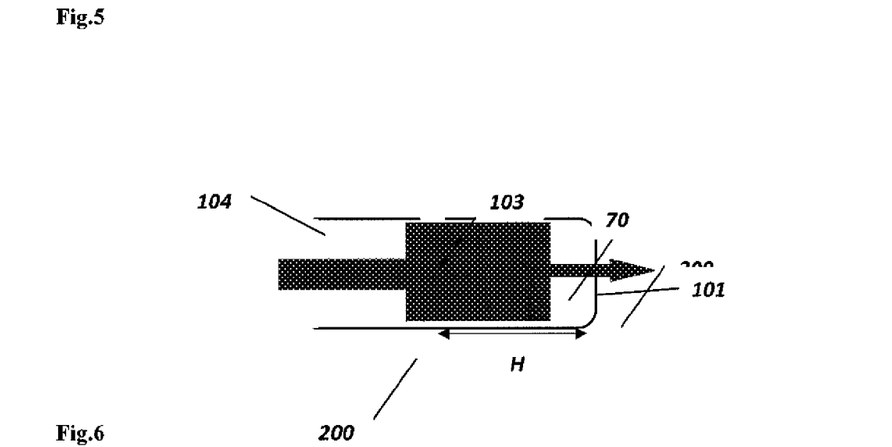
FIG. 5 shows a schematic view of an embodiment in accordance with the present invention.
Figure 6:
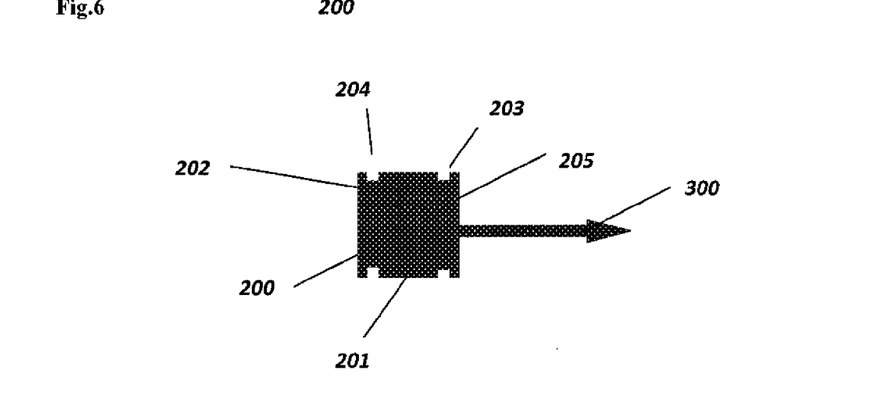
FIG. 6 shows a view of a piston in accordance with the present invention.

In accordance with the embodiments above, more preferably, in order to make all the liquid flow from the piston cavity 70 into the test chamber 10 to achieve contact with the test component 20 in the test chamber, it is necessary to ensure that each final yield of the liquid sample in the device equals the test chamber in volume, and the thickness h* of the piston 200 (or the length of the outer edge of the piston 201) virtually equals the length or depth h of the piston cavity 70. Thus, when the piston 200 is at its initial position, the outer edge 205 of the piston is near the opening 103 between the piston cavity 70 and the collecting chamber 80 (see FIG. 4), or the outer edge semi-seals the opening, so that the liquid sample can flow smoothly from the collecting chamber into the piston cavity. If there is liquid sample in the collecting chamber, e.g. urine, when the piston is at the first position, the entire piston 200 is located on one side of the opening and inside the piston chamber 100. As the piston is pushed, once the outer edge 201 of the piston seals the opening 103, the puncturing component 300 inside the piston cavity pierces the sealing material 900 that seals the other end 101 of the piston chamber 100; or the push rod inside the piston cavity pushes open the sealing lid (silica gel lid) that seals the other end 101 of the piston chamber. At this moment, the liquid sample flows from the piston cavity 70 into the test chamber. At the same time, the liquid sample in the collecting chamber 80 can no longer return to the piston cavity 70. As the piston continues to move inside the piston cavity, as a matter of fact, the volume of the piston cavity has been gradually reduced, and the piston 200 can press all the liquid from the piston cavity 70 into the test chamber. While compressing the piston cavity 70, the outer edge 201 of the piston keeps sealing the opening 103 with the piston cavity 70, so that the liquid sample cannot return from the collecting chamber to the piston cavity 70 (see FIG. 5). To make sure that the piston 200 can keep sealing the opening 103 during its motion, we can carve one or two grooves 204 and 205 on the outer edge 201 of the piston, and set resilient sealing rings 501 and 502 in the grooves. When the piston 200 moves to the bottom of the piston cavity 70 (i.e., the other end 101 of the piston chamber), the resilient sealing components 501 and 502 are stuck on both sides of the opening 103, and thus increasing the sealing effectiveness of the piston.

As Compared to similar traditional designs, embodiments of the present invention can achieve a more precisely quantification result. For example, as described in the U.S. Pat. No. 7,270,958, the volume of the piston cavity 216 is fixed. After the opening between the piston cavity and the collecting chamber 208 is sealed, the piston cavity overall moves to the next position. Even so, some of the liquid sample can flow from the piston cavity into the test chamber 300, but the quantity is not accurate, because the test chamber can be in a confined state sometimes (to prevent the liquid in the test chamber from leaking outside the device). Therefore, the liquid inside the piston cavity needs to overcome the pressure from the test chamber, and cannot flow into the test chamber entirely and naturally. However, as the piston in the present invention compresses the volume of the piston cavity, which can virtually force all the liquid sample to flow from the piston cavity into the test chamber, so the present invention improves the traditional designs by making the sampling more precise. In addition, the present invention not only quantifies accurately, but also makes the piston move fast in the piston chamber, so as to reduce the friction between the piston and the piston chamber and save operational efforts. Further, the traditional piston cavity moves in whole, which requires sealing the piston and the inner wall of the piston chamber so as to prevent the liquid from leaking. For this purpose, it is necessary to increase the force between the piston and the piston chamber, which inevitably adds the forces to push the piston, and make the operation more difficult. In practical operation of the product, when the operator needs to continuously operate multiple devices, it is important that he/she should apply the least force possible. An embodiment of the present invention starts from the defects of traditional designs, adopts completely different ideas, reduces the force exerted on the piston, and improves the operational efficiency and the accuracy of sample loading.

In accordance with other preferred embodiments, when designing the opening 103 or passage between the collecting chamber and the piston cavity, the size is also an important consideration. If the opening is designed too small, it will be difficult for the liquid to flow smoothly from the collecting chamber into the piston cavity due to the surface tension, and thus the piston cavity will not be filled, or bubbles will be present in the piston cavity. If it is too large, it will be difficult to seal the outer edge of the piston. Results from tests prove that 5-8 mm is optimal for the opening of the piston in width.

Figure 2:
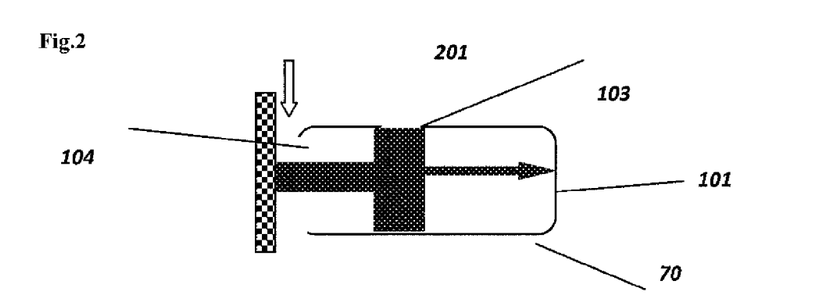
FIG. 2 shows a schematic structural view of another embodiment in accordance with the present invention (the piston is at the second position, sealing the opening, and pierces the other end of the piston chamber)
Figure 3:
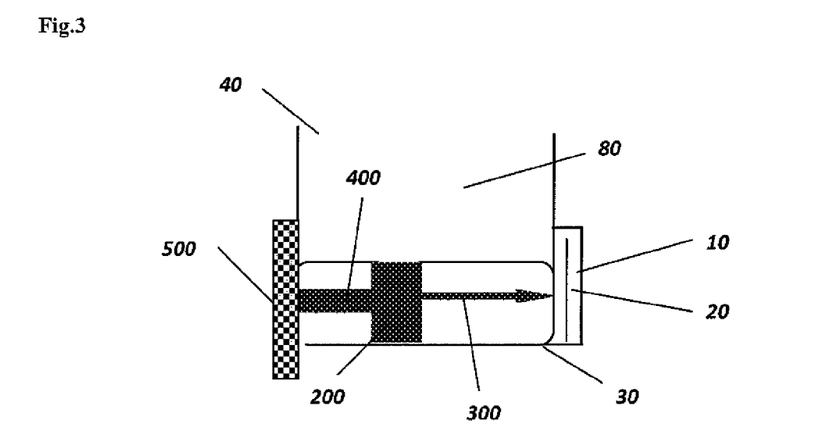
FIG. 3 shows a sectional structural view of another embodiment in the present invention.

In order to maintain the piston stably at the first position, instead of motioning or moving freely inside the piston cavity 70, or allowing sample collecting personnel to mistakenly push the piston in advance, a push rod 400 is set on one end 202 of the piston. This push rod is integrated with the piston. A snap joint 600 is set on the push rod, to maintain the piston stably at the first position, and to maintain the opening 103 stably in the state of open. Preferably, a push cap 500 is set on the piston push rod, with a width larger than the diameter of the piston. During the operation, remove joint 600, push the push cap 500 to get the piston to move inside the piston chamber. Once it moves for an appropriate distance, as the diameter of the push cap is larger than that of the piston, the push cap can only be pushed till the opening on one end of the piston chamber. Thus, the distance that the piston can cover in the piston chamber is restrained by the piston rod and the push cap distance (see FIGS. 1-3).

Figure 11A:
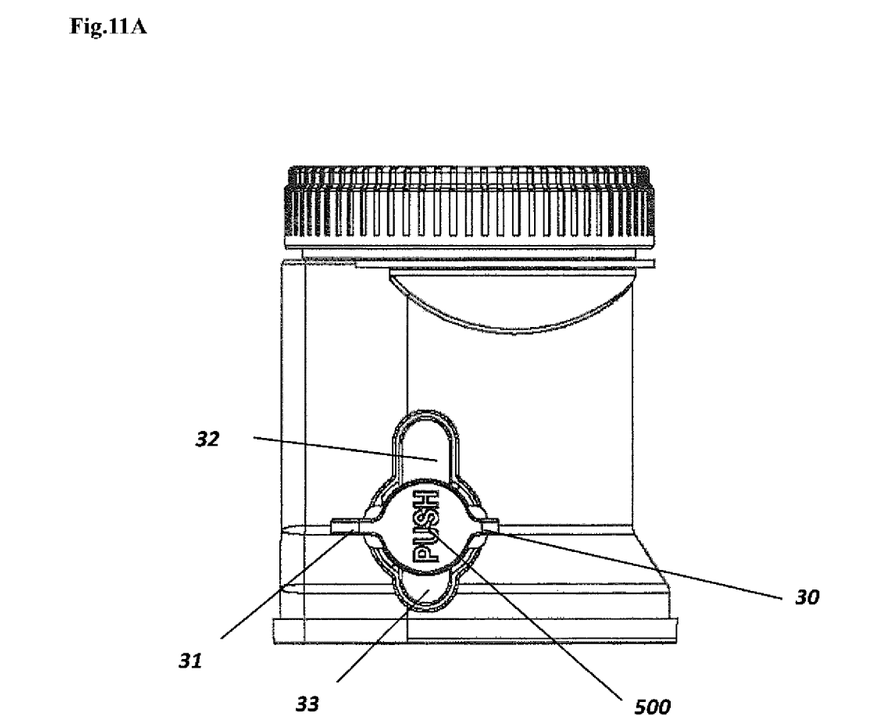
FIGS. 11A and 11B show 3D structural views, with push cap in different rotational positions, of a test device from another specific embodiment in accordance with the present invention.
Figure 11B:
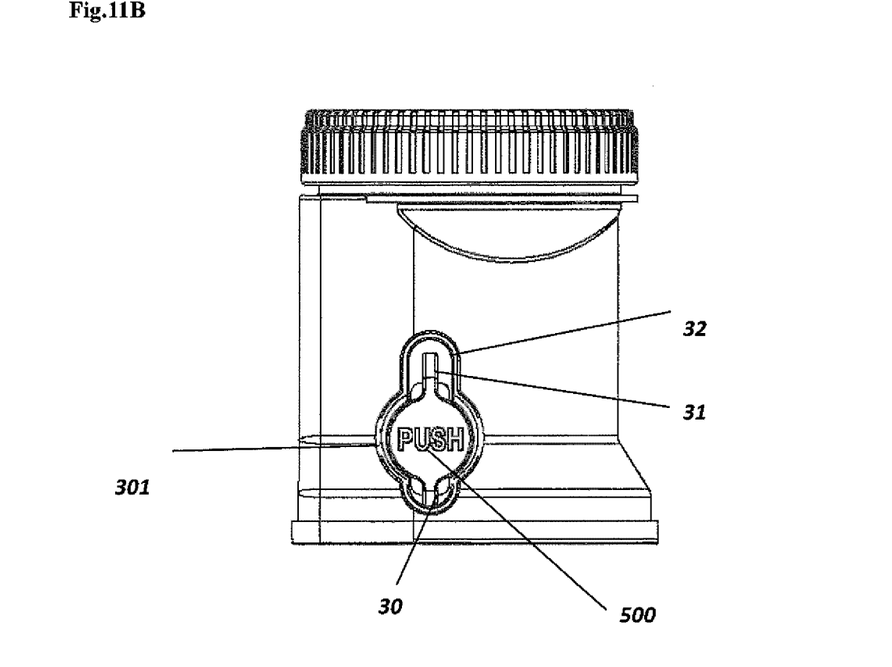

In accordance with other embodiments, as shown in FIGS. 11A-11B, the piston position is not restrained with a block but by setting a pair of opposing bumps 31 and 30 on the push cap, one of which is slightly longer, and the other is shorter. At the position vertical with the bumps, we open two grooves 31 and 32 with certain depth on the outer wall of the piston chamber. These grooves should suit the height of the bumps. When the piston cap is at the initial position, the bumps are stuck on the outer wall of the piston chamber and cannot be easily pushed forward. So, when it is necessary to push the piston, turn 90 degrees, clockwise for example, to lead the taller bumps to the groove 32, and the shorter bump 30 will be located oppositely with the groove 33, then push the piston cap, so as to cause the piston to move inside the piston chamber. In order to prevent the sample collecting personnel to operate in advance, we can affix a seal onto the piston cap; thus, once the seal is torn off, the piston is set in motion, which indicates that the sample collecting personnel may have pushed the piston in advance, and the credibility of the test result is compromised. Then, we will need to re-collect a new sample, which is particularly useful in drug test.

In accordance with some preferred embodiments, the piston, piston push rod, push cap, the puncturing component (or the push rod) or the bumps of the piston cap can be molded once for all. The grooves on the wall of the piston chamber and the piston chamber can also be molded once for all by injection molding.

Collecting Chamber, Test Chamber and Piston Chamber

The collecting chamber 80 is a chamber structure used for collecting liquid samples. The collecting chamber can share a wall with the piston chamber, or the piston chamber can lie below the bottom of the collecting chamber and maintains liquid communication with the collecting chamber through the opening 103. The collecting chamber 80 has an opening, which can be sealed by a lid. The volume of the collecting chamber can be set at will between 100 and 500 mm. The test chamber 10 is located outside of the collecting chamber, and the test component 20 can be set inside the test chamber. The collecting chamber and the piston chamber of the present invention as well as the position of the test chamber can be set as in traditional configurations. For example, the installation position as described in the U.S. Pat. Nos. 6,576,193 and 7,270,959 can serve as some specific embodiments of the present invention. In addition, the manufacturing materials for these parts are produced with known plastic materials in this industry. You may refer to the detailed descriptions as in the U.S. Pat. No. 7,270,959 for the settings of the test chamber, the collecting chamber and test components. As part of the present invention, when the test component is set inside the test chamber, the test chamber can be transparent. Thus, the test result on the test strip can be read through the transparent test chamber.

Figure 7:
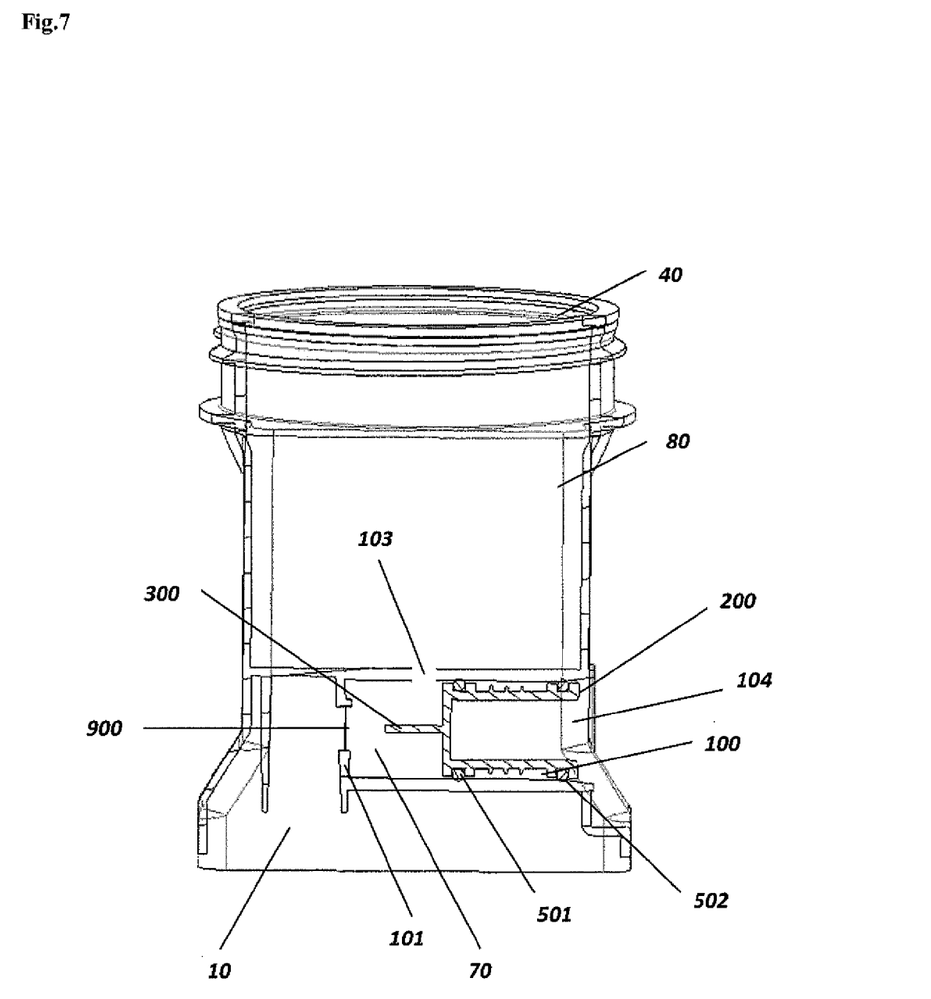
FIG. 7 shows a sectional structural view of a test device from a specific embodiment of the present invention.

In accordance with a preferable embodiment, for example FIG. 7, a device consists of a collecting chamber 80 with an opening 40 that can be sealed by lid 2. The way that the lid seals the opening can be in threaded structure or the form of a bolt. At the bottom of the collecting chamber, there is an opening 13, which remains a liquid communication with the piston chamber. At the other end 103 of the piston chamber 100, there is an opening, which is sealed by the sealing material 900. Such sealing material is puncturable, such as film, aluminum foil and double-sided adhesive, etc. The puncturing component 300 is integrated with the piston 200. On the outside of the other end 103 of the piston chamber is the test chamber. We set test components inside the test chamber, grooves on the piston, and resilient sealing rings 501 and 502 in the grooves. The piston 200 is set on one end of the piston chamber 104. When the piston is located at the initial position, the end with the puncturing component is inside the piston cavity 70, but it does not seal the opening 103. If any liquid sample is collected in the collecting chamber 80, under the gravity, the liquid sample will naturally flow into the piston cavity. So, at this time, if it is necessary to perform a test, it is advisable to preset joint 600 on the piston rod, push the piston 200 to move toward the other end 101 of the piston chamber. As the opening 103 is sealed, the puncturing component pierces the sealing material 900. At this time, as the opening is sealed, the liquid sample inside the collecting chamber cannot flow back to the piston cavity. In the meanwhile, since the puncturing component pierces the sealing material 900, the liquid sample inside the piston cavity is released into the test chamber and contacts the test component, so as to complete the test on the analyte in the liquid sample. In order to get the liquid sample to flow from the piston cavity into the test chamber more smoothly, the piston continues to move after seating the opening 103, compresses the volume of the piston cavity, and forces all the liquid sample to flow from the piston cavity into the test chamber, so as to complete quantifying the liquid sample accurately.

Figure 8:
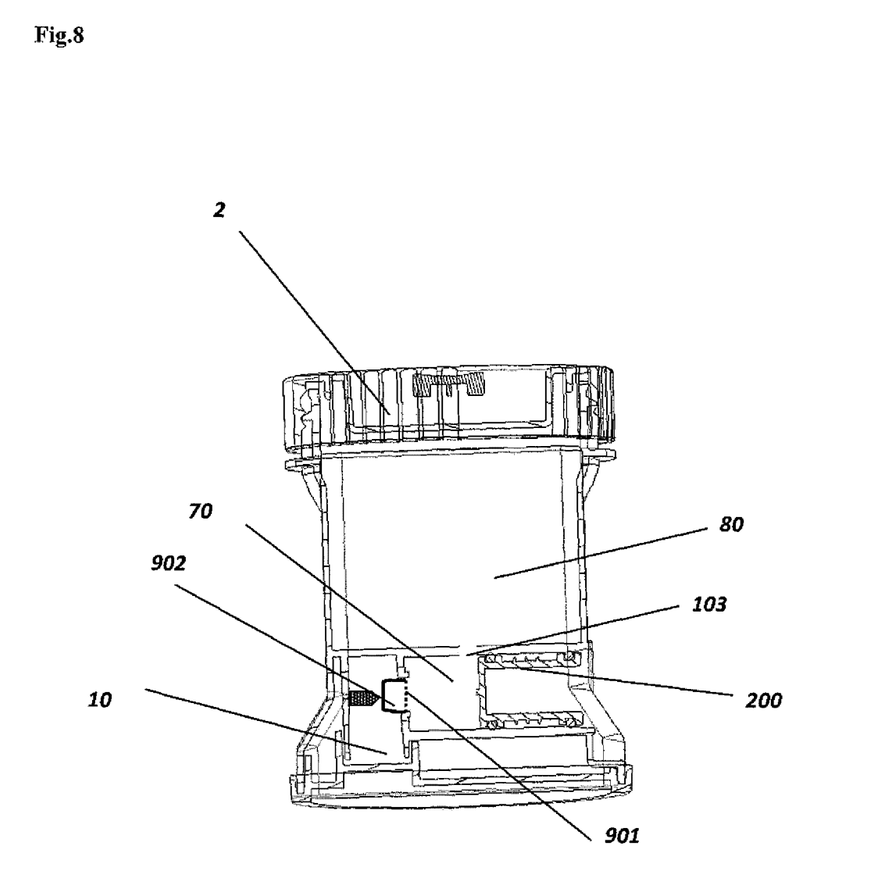
FIG. 8 shows a sectional structural view of a test device from another specific embodiment the present invention.

In accordance with another embodiment, for example FIG. 8, a device includes a collecting chamber 80, which has an opening 40 that can be sealed by the lid 2. The way that the lid seals the opening can be in threaded structure or the form of a bolt. At the bottom of the collecting chamber, there is an opening 13, which remains a liquid communication with the piston chamber. At the other end 103 of the piston chamber 100, there is an opening, which is sealed by the sealing material 900. Such sealing material is resilient and puncturable, such as rubber film and plastic film. On the outside of the other end 103 of the piston chamber, opposite to the sealing material, we set a puncturing component. At this moment, the puncturing component is not inside the piston chamber, but outside the piston chamber instead. On the outside of the other end 103 of the piston chamber is the test chamber. We set test components inside the test chamber, grooves on the piston, and resilient sealing rings 501 and 502 in the grooves. The piston 200 is set on one end of the piston chamber 104. When the piston is located at the initial position, the puncturing component is close to the sealing material, but without any contact. At this moment, the piston is on the side of the opening 103, but not sealing the opening 103. If any liquid sample is collected in the collecting chamber 80, under the gravity, the liquid sample will naturally flow into the piston cavity. So, at this time, if it is necessary to perform a test, it is advisable to preset a snap joint 600 on the piston rod, push the piston 200 to move toward the other end 101 of the piston chamber. As the opening 103 is sealed, the puncturing component pierces the sealing material 900. At this time, as the opening is sealed, the liquid sample inside the collecting chamber cannot flow back to the piston cavity. In the meanwhile, since the puncturing component pierces the sealing material 900, the liquid sample inside the piston cavity is released into the test chamber and contacts the test component, so as to complete the test on the analyte in the liquid sample. At the same time when the piston sealing is opened, as the piston continues to move inside the piston cavity, the air pressure inside the piston cavity increases, which forces the resilient sealing film to bloat outwardly. Once the bloated resilient film contacts the puncturing component, it is pierced, and releases the liquid sample into the test chamber. In order to get the liquid sample to flow from the piston cavity into the test chamber more smoothly, the piston continues to move after sealing the opening 103, compresses the volume of the piston cavity, and forces all the liquid sample to flow from the piston cavity into the test chamber, so as to complete quantifying the liquid sample accurately.

Figure 9:
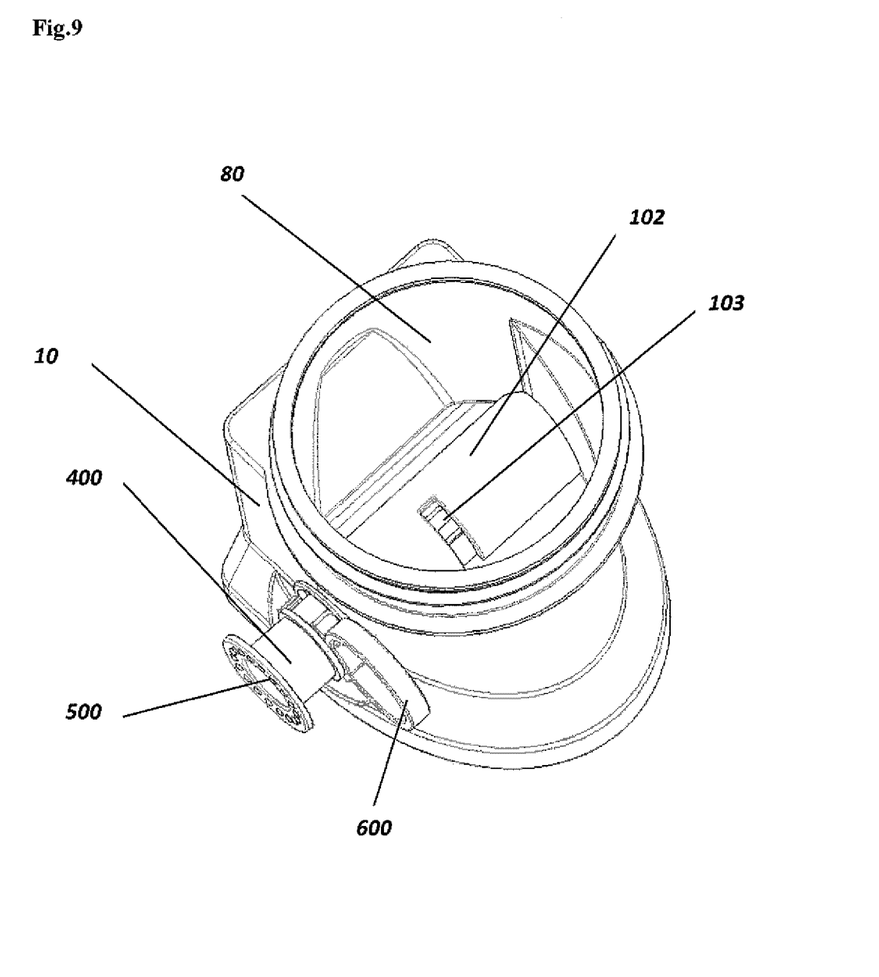
FIG. 9 shows a 3D structural view of a test device from another specific embodiment in accordance with the present invention.

In accordance with another embodiment, as shown in FIG. 9, apart from the same embodiments as shown in FIG. 7, the difference is: we set a piston push rod 400 integrated with the piston, and set a push cap 500 on the piston push rod. The piston chamber 100 lies at the bottom of the collecting chamber, and an opening 103 is made on the wall of the piston, with a width of 3-8 mm. In the meanwhile, we set a snap joint 600 on the piston push rod, to maintain the piston to stably stay at the initial first position inside the piston chamber, that is, not to seal the opening 103. During the operation, remove the snap joint 600, push the push cap 500 to get the piston to move inside the piston chamber. At the same time when the piston seals the opening, it forces the liquid sample to flow from the piston chamber into the test chamber. The way to enter into the test chamber can be any of the specific embodiments as shown in FIGS. 1-8. For example, the puncturing component pierces the sealing material, or the push-out component pushes out the sealing cap, or makes the sealing material resilient, and sets the puncturing component outside the piston cavity. Of course, in order to get the liquid sample to flow from the piston cavity into the test chamber more smoothly, the piston continues to move after sealing the opening 103, compresses the volume of the piston cavity, and forces all the liquid sample to flow from the piston cavity into the test chamber, so as to complete quantifying the liquid sample accurately.

Figure 10:
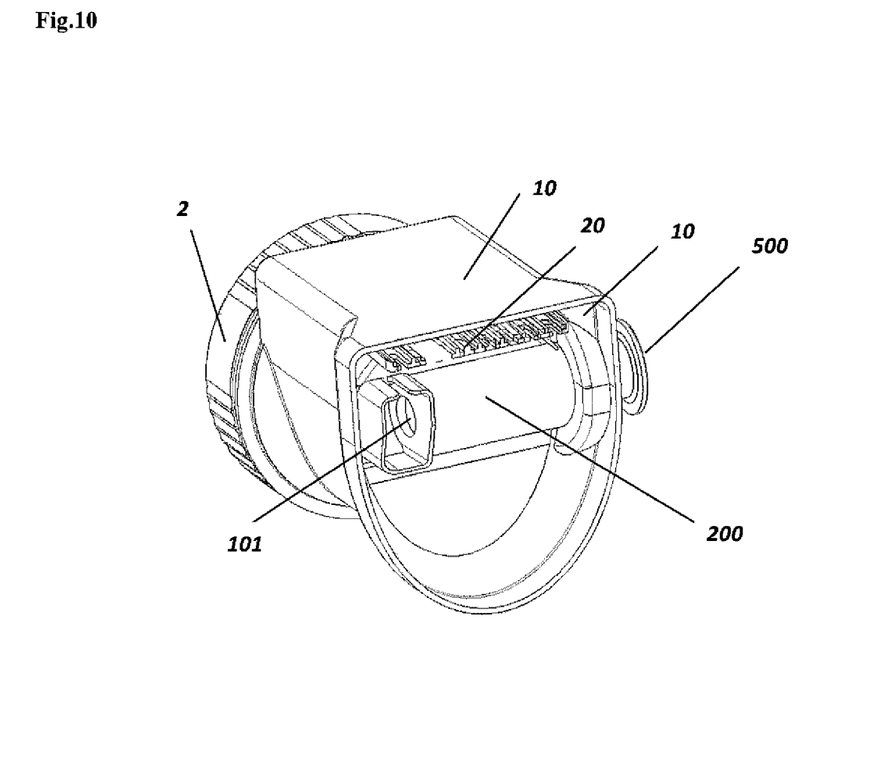
FIG. 10 shows a 3D structural view of a test device from another specific embodiment in accordance with the present invention.

In accordance with another embodiment, e.g., FIG. 10, apart from the same embodiments as shown in FIG. 7, the difference is: there is an opening on the end 101 of the piston chamber. On this opening, we set a sealing plug (such as a silica gel plug) to seal the opening. Meanwhile, we set a rod on the piston, which moves along with the piston. When the outer edge 201 of piston seals the opening 103, the push-out rod pushes the plug into the test chamber, and releases the liquid sample from the piston cavity into the test chamber. The liquid sample contacts the test component and completes the test of the analyte. In order to get the liquid sample to flow from the piston cavity into the test chamber more smoothly, the piston continues to move after sealing the opening 103, compresses the volume of the piston cavity, and forces all the liquid sample to flow from the piston cavity into the test chamber, so as to complete quantifying the liquid sample accurately.

Specific Embodiments

We hereby describe specific embodiments of the present invention together with attached drawings in details. Such description should not serve as limitations to the Claims in any manner, but serve to explain how to implement embodiments of the present invention.

Specific Example

One thousand (1000) products are produced by the method as disclosed in the U.S. Pat. No. 7,270,959, and another 1000 devices of the present invention. The collecting chamber of U.S. Pat. No. 7,270,959 (the '959 product), with the volume of 450 ml, contains a liquid sample of 25 ml, so does the device of the present invention. In addition, the collecting chamber is the same as the piston chamber in the opening size and location as well as volume. Each device is filled with water or urine sample of 300 ml, which shall be operated in manner described, respectively, to put the piston in three statuses by comparing to U.S. Pat. No. 7,270,959. The design of piston in the present invention is different from that in U.S. Pat. No. 7,270,959, and their operating modes substantially vary as well. Meanwhile, it is necessary to compare differences in the volume of the sample transferred into each test chamber and operation duration.

TABLE 1

Comparison on device parameters between
the present invention and another product

|  | Leakage ratio | Volume of urine in test chamber | Volume of water in test chamber | Volume of liquid in piston cavity | Time of operation |
|---|---|---|---|---|---|
| '959 product | 20/1000 | 24.7 ml (average) | 14.3 ml (average) | 23.2 ml (average) | 2.3 s |
| The present invention | 12/1000 | 24.3 ml (average) | 23.8 ml (average) | 24.8 ml (average) | 1.5 s |

It is particularly noted that the volume of urine that actually reaches the test chamber vary in a wide range. Among the 1000 urine cups, 300 of them have 14-18 ml of liquid actually reach the test chamber, 450 of them have 23-24.5 ml, and 250 have 12-13.5 ml, indicating that the volumes of the urine actually reaching the test chambers, varying considerably, is difficult to measure, thus causing great differences to the test results. However, the present invention has made certain improvement, and achieved a result that about 950 urine cups having 22-24 ml reaching the test chamber, with about 50 having 20-21.5 ml.

TABLE 2

Comparison on degree of comfort and push force between
the present invention and another product

|  | Push force on piston | Degree of comfort |
|---|---|---|
| '959 product | 200.4 Newton | 200(10 points), 300 (8 points), 400 (6 points), 100 (3 points) |
| Present invention | 120.45 Newton | 400 (10 points), 500 (8 points), 80 (6 points), 20 (3 points) |

The degree of comfort has been ranked based on the operation by over 1000 ordinary operators, with ranking standard as follows: 10 points—the most comfortable; 8 points—comfortable; 6 points—average; 3 points—uncomfortable.

What is claimed is:

1. A device for testing an analyte in a liquid sample, comprising:
    a test chamber used to contain test components;
    a collecting chamber used to collect liquid sample;
    a piston chamber between the test chamber and the collecting chamber;
    a piston with two ends, wherein the piston is disposed in the piston chamber;
        wherein the piston chamber has a first opening and a second opening,
        wherein the first opening, located between the collecting chamber and the piston chamber, is sealed by the piston when the piston is in a second position, and
        wherein the second opening is sealed by a sealing material that is resilient and puncturable,
    a puncturing component disposed on the device outside the piston chamber and pointing at the sealing material,
    wherein when the piston moves from a first position to the second position, the first opening is sealed and continued movement of the piston makes the sealing material bulge outwardly, thereby causing the puncturing component to pierce the sealing material to release the liquid sample into the test chamber.

2. The device according to claim 1, wherein the resilient and puncturable material is air tight.

3. The device according to claim 2, wherein the resilient and puncturable material is a latex, rubber or plastic film.

* * * * *